United States Patent [19]

Kistner et al.

[11] Patent Number: 5,753,489
[45] Date of Patent: May 19, 1998

[54] METHOD FOR PRODUCING VIRUSES AND VACCINES IN SERUM-FREE CULTURE

[75] Inventors: Otfried Kistner, Vienna; Noel Barrett, Klosterneuberg/Weidling; Wolfgang Mundt; Friedrich Dorner, both of Vienna, all of Austria

[73] Assignee: IMMUNO AG, Vienna, Austria

[21] Appl. No.: 487,046

[22] Filed: Jun. 7, 1995

Related U.S. Application Data

[63] Continuation-in-part of Ser. No. 338,761, Nov. 10, 1994, abandoned.

[51] Int. Cl.$^6$ .......................... C12N 7/02; A61K 39/145
[52] U.S. Cl. .................... 435/235.1; 424/209.1
[58] Field of Search .................. 435/235.1; 424/209.1

[56] References Cited

U.S. PATENT DOCUMENTS

| 4,072,565 | 2/1978 | Weiss et al. | 435/172.3 |
|---|---|---|---|
| 4,205,131 | 5/1980 | Almeida | 435/235.1 |
| 4,500,513 | 2/1985 | Brown et al. | 424/209.1 |
| 4,525,349 | 6/1985 | Montagnon et al. | 424/217.1 |
| 4,664,912 | 5/1987 | Wiktor et al. | 424/224.1 |
| 4,783,411 | 11/1988 | Gabliks | 435/237 |
| 4,927,762 | 5/1990 | Darfler | 435/387 |
| 5,147,790 | 9/1992 | Wilson | 435/70.3 |
| 5,316,938 | 5/1994 | Keen et al. | 435/404 |
| 5,391,491 | 2/1995 | Mundt et al. | 435/349 |
| 5,393,668 | 2/1995 | Cinatl et al. | 435/402 |

FOREIGN PATENT DOCUMENTS

| 0019218 | 11/1980 | European Pat. Off. . |
|---|---|---|
| 0113665 | 7/1984 | European Pat. Off. . |
| 0485689 | 5/1992 | European Pat. Off. . |
| 0115442A2 | 8/1994 | European Pat. Off. . |
| WO 91/03552 | 3/1991 | WIPO . |
| WO 91-09937 | 7/1991 | WIPO . |
| WO 91/09937 | 7/1991 | WIPO . |

OTHER PUBLICATIONS

Cinatl et al. Archives of Virology, 125: 327–330 (1992).
Cinatl et al. Intervirology 37: 361–366 (1994).
Cinati et al. Biology International, vol. 17: No. 9 (1993).
Nakamura et al. J. Gen Virol. 56: 199–202 (1981).
Lau et al. Virology 212: 225–231 (1995).
Merten et al. Cytotechnology 14: 47–59 (1994).
Merten et al. Biologicals 23: 185–189 (1995).
Swanson et al. Journal of Biological Standardization 16: 311–320 (1988).
Levenbrook et al. Journal of Biological Standardization 12: 391–398 (1984).
Contreras et al. In Vitro Cellular & Developmental Biology 21(11):649–652 (1985).
Johnson et al. Develop. biol. Standard. 50:27–35 (1982).
Katz et al. The Journal of Infectious Diseases 160(2): 191–198 (1989).
Kaverin et al. The Journal of Virology, 69(4):2700–2703 (1995).
Govorkova et al. The Journal of Infectious Diseases 172: 250–253 (1995).
Bulletin of the World Health Organization 73(4): 431–435 (1995).
Vincent–Falquet et al. Develop. biol. Standard. 70: 153–156 (1989).
Luytjes et al. Cell 59: 1107–1113 (1989).
Robertson et al. Journal of General Virology 72: 2671–2677 (1991).
Scild et al. Nature 303: 706–709 (1983).
Klenk et al. "The Molecular Biology of Influenza Virus Pathogenicity", pp. 247–281, Academic Press (1988).
Edsall et al. "Requirements For Inactivated Influenza Vaccine", WHO: Technical Report Series, 384:41–56 (1968).
Mayr et al. "Vergleichende Studien über die Züchtung ... ", pp. 72–102 (1961).
Steineke–Gröber et al. "Influenza virus hemagglutinin with multibasic cleavage site is activated by furin . . . ", The EMBO Journal, 11:2407–2414 (1992).
Lazarowitz et al. Enhancement of the Infectivity of Influenza A and B Viruses by Proteolytic Cleavage . . . , Virology, 68:440–454 (1975).
Hirst "The Agglutination Of Red Cells By Allantoic Fluid Of Chick Embryos Infected With Influenza Virus", Science, 94:22–23 (1941).
Barrett et al. "Viruses", Methods of Immunological Analysis 2:115–132 (1993).
Scholtissek et al. "Multiplication of Influenza A Viruses with Cleavable and Non–cleavable Haemagglutinin . . . ", J. Gen. Virol., 69:2155–2165 (1988).
Barr "Mammalian Subtilisins: The Long–Sought Dibasic Processing Endoproteases", Cell, 66:1–3 (1991).

(List continued on next page.)

*Primary Examiner*—James Ketter
*Assistant Examiner*—John S. Brusca
*Attorney, Agent, or Firm*—Foley & Lardner

[57] ABSTRACT

A method for producing Influenza and other viruses and vaccines derived therefrom utilizes serum-free cultured vertebrate cells or vertebrate biomass aggregates to both eliminate the necessity to use costly methods requiring whole chicken embryos and, optionally, to provide proteases suitable for the activation of a wide variety of viruses. In one aspect, the method comprises the periodic or continuous removal of "treatment portions" of virus-containing culture medium into an "augmentation loop" for treatment with a broad range of substances, such as proteases that augment the activation of the virus. Use of the loop allows utilization of such substances at high concentrations while eliminating their cell toxic effects. Another aspect of the invention provides for the alteration of cleavage sites in virus proteins to thereby render them more susceptible to activation in culture. Thus, the method provides for the high yield production of many viruses that can be easily scaled up to continuous large scale production volumes and for resultant vaccines which are free of egg proteins and are much more economical to produce.

8 Claims, No Drawings

OTHER PUBLICATIONS

Burnet "Influenza Virus Infections Of The Chick Embryo By The Amniotic Route", *Austr. Jnl. Experimental Biology and Medical Science.* 18:353–360 (1940).

Tomas et al. Rev. Roum. Med. Virol., 32(2):145–154, 1981.

Boehringer Mannheim Biochemicals catalog pp. 191–195, 1994.

Vey et al. Hemagglutinin activation of pathogenic avian influenza viruses of serotype H7 requires the protease recognition motif R-X-K/R-R Virology vol. 188 408–413, 1992.

Enami et al. Introduction of site-specific mutations into the genome of influenza virus Proc. Natl. Acad. Sci. U.S.A. vol. 87, 3802–3805

METHOD FOR PRODUCING VIRUSES AND VACCINES IN SERUM-FREE CULTURE

The present application is a continuation-in-part of application Ser. No. 08/338,761, filed Nov. 10, 1994, now abandoned, entitled "Method for Producing Influenza Virus and Vaccine." U.S. application Ser. No. 08/338,761 is incorporated herein by reference.

FIELD OF THE INVENTION

The present invention relates to means and methods for increasing the yield and efficiency of virus production in cell cultures and vaccines derived therefrom. The present invention also relates to means and methods for controlling the infectivity of viruses.

BACKGROUND OF THE INVENTION

Efficient vaccine production requires the growth of large quantities of virus produced in high yields from a host system. Different types of virus require different growth conditions in order to obtain acceptable yields. The host in which the virus is grown is therefore of great significance. Thus, depending upon the virus type, a virus may be grown in primary tissue culture cells, established cell lines or in embryonated eggs, such as those from chickens.

The cultivation conditions under which a virus strain is grown also are of great significance with respect to achieving an acceptably high yield of the strain. Thus, in order to maximize the yield of a desired virus strain, both the host system and the cultivation conditions must be adapted specifically to provide an environment that is advantageous for the production of a desired virus strain. Therefore, in order to achieve an acceptably high yield of different virus strains, a system which provides for easy and rapid adaptation of both the host system and the cultivation conditions is required. This is particularly true in view of the natural and commonplace changes in virus strain genomes and the consequent change in virus serotypes.

With time, many viruses change their serotypes. Any change in virus serotype requires a corresponding change in a vaccine directed toward producing immunity toward that virus serotype. Consequently, to maintain the efficiency of the protection accorded by a vaccine to a particular new virus serotype, a new vaccine must be produced which confers immunity to that new serotype. In order to produce the new vaccine, the new virus strains must be grown.

In many cases, the optimum growth conditions for the new virus strains are different from the conditions employed to grow their predecessors. Hence, a cultivation system that can be easily adjusted to provide the requirements for optimum growth of new virus strains is highly desirable. Moreover, practical considerations, such as the need for high production output of the new strain, render highly desirable a method that is applicable to large scale production of the virus.

One typical example of a virus that changes its serotype frequently is Influenza virus. Influenza is a major respiratory disease in man and is responsible for many thousands of deaths every year.

There are three general types of Influenza viruses, Type A, Type B and Type C. The types are defined by the absence of serological crossreactivity between their internal proteins. Influenza Type A viruses are further classified into sub-types based on antigenic differences of their glycoproteins, the hemagglutinin (HA) and neuraminidase (NA) proteins.

Humans are susceptible mainly to diseases caused by infection with Influenza Types A, B, and C viruses.

Currently, the most significant causes of Influenza infections in humans are those attributable to Type B and to subtypes H1N1 and H3N2 of Influenza Type A. Accordingly, antigens of Type B and of subtypes H1N1 and H3N2 of Influenza Type A are those which are generally incorporated into present Influenza vaccines. The vaccines currently available have protection rates ranging from 75–90%.

The Influenza HA antigen is the major target for the protective immune responses of a host to the virus. One of the problems in the development of effective Influenza vaccines stems from the high mutation rate of the gene coding for the HA protein, resulting in frequent changes in its antigenicity. Therefore, in order to produce effective vaccines, new vaccines from recent Influenza isolates must be produced frequently.

The normal practice of recovering new viral isolates involves recovery with a throat swab or similar source, followed by cultivation of the isolates in embryonated chicken eggs. Although the initial isolation into eggs may be difficult, the virus adapts to its egg host, and large scale production of the virus can be carried out in eggs.

Conventional methods for producing Influenza vaccine have always involved the growth of the viruses in embryonated chicken eggs. Viruses grown by this method are then used for producing live attenuated virus, killed whole virus or subunit vaccines. However, conventional methodology involving embryonated chicken eggs to produce Influenza vaccine is extremely cumbersome, involving the handling of many thousands of eggs per week. In a typical operation, eggs must be candled, the shell must be sterilized and each egg must be inoculated by injection of a small volume of virus into the allantoic cavity. The injected eggs are then incubated for 48–72 hours at 33°–37° C., candled again, refrigerated overnight and opened to allow harvesting of the allantoic fluid. The harvested fluid must then be clarified by filtration and/or centrifugation before processing for further purification. Extensive purification is then required to ensure freedom from egg protein. *Requirements For Inactivated Influenza Vaccine*, World Health Organization Technical Report Series, 384 (1966).

In a typical chicken embryo operation, between one and two eggs are required to produce one dose of Influenza vaccine. Thus, to produce a million doses of vaccine, more than a million egg embryos must be processed. In sum, conventional technology for producing Influenza virus vaccines involves many steps which are difficult to automate and are, accordingly, labor intensive, time consuming, expensive and subject to contamination. Thus, a need exists for methods which are less labor intensive, require less biological tissue per dose produced and are less susceptible to contamination.

Many attempts have been undertaken previously in the art to utilize standard tissue culture technology with primary chicken embryo cells ("CEC") or established mammalian cell lines for Influenza virus vaccine production. These attempts have proven unsuccessful because of the failure of a large number of viral strains to replicate in conventional CEC cultures. The use of established mammalian cell lines such as MDCK has been more successful in replicating some strains. However, a number of virus strains will not replicate in the MDCK line. Another disadvantage of MDCK relates to its transformed nature. Fears about possible adverse effects of the use of transformed cells for human vaccine production make MDCK a disfavored cell line for human vaccine production.

One of the primary difficulties in growing a number of Influenza strains in primary tissue culture or established cell lines arises from the necessity for proteolytic cleavage activation of the Influenza hemagglutinin in the host cell. Cleavage of the virus $HA_o$ precursor into the HA 1 and HA 2 subfragments is a necessary step in order for the virion to infect a new cell. Thus, cleavage is required in order to convert new virus particles in the host cells into virions capable of infecting new cells. Cleavage is known to occur during transport of the integral $HA_o$ membrane protein from the endoplasmic reticulum of the infected cell to the plasma membrane. In the course of transport, hemagglutinin undergoes a series of co- and post-translational modifications including proteolytic cleavage of the precursor HA into the amino-terminal fragment HA 1 and the carboxyterminal HA 2.

The fact that Influenza virions have been found which contain either uncleaved or cleaved HA glycoproteins indicates that cleavage is not always necessary for virus assembly and release from the infected cell. Cleavage of HA is indeed necessary, however, for the initiation of infection of a new host cell.

Although it is known that an uncleaved HA can mediate attachment of the virus to its neuramic acid-containing receptors at the cell surface, it is not capable of the next step in the infectious cycle, which is fusion. It has been reported that exposure of the hydrophobic amino terminus of the HA 2 by cleavage is required so that it can be inserted into the target cell, thereby forming a bridge between virus and target cell membrane. This is followed by fusion of the two membranes and entry of the virus into the target cell.

Proteolytic activation of hemagglutinin follows a pattern observed with many enzymes and hormone precursors, such as proinsulin, progastrin and proopiomelanocortin. It involves cleavage at an arginine residue by a trypsin-like endoprotease. The available evidence suggests that the endoprotease is an intracellular enzyme which is calcium dependent and has a neutral pH optimum. However, beyond these observations, little is known about the nature of the intracellular protease (Klenk et al, "The Molecular Biology of Influenza Virus Pathogenicity", *Adv. Virus Res.*, 34:247–281 (1988)).

Since the activating proteases are cellular enzymes, the infected cell type determines whether the Influenza hemagglutinin is cleaved. The hemagglutinins of the mammalian Influenza viruses and the nonpathogenic avian Influenza viruses are susceptible to proteolytic cleavage only in a restricted number of cell types. On the other hand, the hemagglutinins of pathogenic avian viruses among the H 5 and H 7 subtypes are cleaved by proteases present in a broad range of different host cells. Thus, there are differences in host range resulting from differences in hemagglutinin cleavability which can be correlated with the pathogenic properties of the virus.

The differences in cleavability are due to differences in the amino acid sequence of the cleavage site of the hemagglutinin. Sequence analyses have revealed that the HA1 and HA2 fragments of the hemagglutinin molecule of the pathogenic avian and of all mammalian Influenza viruses are linked by a single arginine. In contrast, the pathogenic avian strains have a sequence of several basic amino acids at the cleavage site with the common denominator being lysine-arginine or arginine-arginine. The hemagglutinins of all Influenza viruses are cleaved by the same general mechanism resulting in the elimination of the basic amino acids.

The protease activities which are essential for cleavage of a broad range of Influenza virus strains are available not only in the embryonated egg, but in the system of the present invention. Thus, the system of the present invention allows replication of all strains and their corresponding vaccines. However, conventional CEC cultures prepared from chick embryos will allow replication of only a narrow range of Influenza virus strains. Standard procedures for preparation of CEC cultures involve removal of the head and inner organs and multiple trypsinization steps. These procedures result specifically in the loss of brain, heart, lung, liver and kidney cells, which have been shown to replicate a number of Influenza strains (Scholtissek et al., "Multiplication of Influenza A Viruses with Cleavable and Non-cleavable Hemagglutinin in Chicken Embryo Membranes or Organes, and Cell Cultures Derived Therefrom", *J. Gen. Virol.*, 69:2155–2164 (1988)). Standard procedures thus result in a highly selected cell population consisting mainly of fibroblasts, which are limited in terms of the virus strains that they can support.

The importance of providing a number of different cell types, or cells having a number of different proteases for effective replication of a broad range of viruses is demonstrated by the fact that other approaches also have limitations. For example, the chorio-allantoic membrane (CAM) of the embryonated egg does not support equally the replication of different human Influenza A viruses because the CAM is derived from three general cell layers which have different capabilities to activate the viral HA by proteolytic cleavage.

Improvements in Influenza virus production have been attempted before. For instance, it has been reported that the limited replication of several Influenza A strains in standard CEC cultures could be overcome by the addition of trypsin to the tissue culture medium. Trypsin addition significantly increases the infectivity of various strains grown in CEC cultures (Lazarowitz et al., "Enhancement of the Infectivity of Influenza and B Viruses by Proteolytic Cleavage of the Hemagglutinin Polypeptide", *Virology*, 68:440–454 (1975)). In addition Stieneke-Gröber et al., "Influenza Virus Hemagglutinin with Multibasic Site is Activated by Furin, a Subtilisin- like Endoprotease", *EMBO*, 11:2407–2414 (1992) have identified the HA activating enzyme in MDBK cells as a furin-like protease. Such enzymes have been isolated from human and mouse tissues and constitute a new family of eukaryotic subtilisin-like endoproteases.

U.S. Pat. No. 4,783,411, to Gabliks discusses a method for preparing Influenza vaccines in goldfish cell cultures. The virus particles for infecting the Gabliks cultures after their establishment were obtained from chicken embryo cultures or from infected CD-1 strain mice. The virus is passaged at least twice in such goldfish cell cultures, resulting in an attenuated virus which may be used as a live vaccine.

U.S. Pat. No. 4,500,513 to Brown et al. discloses the production of unmodified virus particles for making vaccine from liquid cell culture or cell monolayer culture wherein a protein hydrolyzing enzyme, such as trypsin, chymotrypsin or carboxypeptidase, is incubated with a partially infected culture to increase the proportion of additional cells infected by the virus and to ensure the maximum cytopathic effect. Harvesting of the virus is performed at a point in the growth phase of the virus which exhibits maximum cytopathic effect. All of the examples of Brown, however, describe a dog kidney cell line that is not usable for human vaccine production. Due to the maximum cytopathic effects of the virus in the method according to Brown et al., virus yield is limited to only one round of virus replication. Moreover, Brown does not teach manipulation of the virus genome nor optimization of culture conditions. Therefore, the method of Brown is not applicable for the large-scale production of virus, which is necessary for the efficient production of corresponding vaccines.

U.S. Pat. No. 4,205,131 to Almeida discloses a method for propagating rotavirus in cell culture in the presence of serum-free medium containing the proteolytic enzyme trypsin. Due to the lethal effect on the cells of trypsin at higher levels, the virus yield of Almeida was limited to that produced in one round of replication. Thus, Almeida does not recognize the advantages which may be obtained by growing cells in serum-free medium for several generations prior to infection by virus. In addition, Almeida does not recognize the advantages attendant to multiple rounds of virus replication.

In the prior art, the use of serum-free medium to grow viruses is known (for example EP 115442, U.S. Pat. No. 4,525,349, U.S. Pat. No. 4,664,912) such that host cells are first grown in serum-containing medium and, just before infection with the respective virus, the serum-containing medium is replaced by serum-free medium. The use of serum-free medium as it is described in the context of the present invention is new and inventive, however.

In view of the limitations of the prior art, there exists a need for safe and effective approaches for the production of viruses, such as Influenza. These approaches should be capable of mass production of virus with materials that are readily available and which require minimal handling.

SUMMARY OF THE INVENTION

It is an object of the present invention to provide for the high yield production of viruses from cell culture and to provide for the production of vaccines from those viruses.

It is a further object of the present invention to provide a method for the continuous production of virus from a sustained culture of vertebrate cells with a minimum of human manipulation.

It is also an object of the present invention to provide a method for optimizing the activity of a virus in culture by augmentation with exogenous substances.

It is also an object of the present invention to provide a method for the high yield production of all types of cellular products, that is, viruses or recombinant proteins or other cellular products, in a very flexible system that can be easily adapted to the specific requirements of the various products.

In accordance with these and other objects, the present invention provides a method for producing viruses comprising the steps of providing a culture of vertebrate cells, growing the cells for more than one generation in medium that is free of serum, infecting the culture with a virus, and incubating the cell culture infected with the virus to propagate the virus into the medium to produce virus-containing medium. Modifications of the method include, after the step of providing a culture of vertebrate cells and before the step of infecting the cells, the vertebrate cells are grown in the medium which is free of serum for at least six generations, for at least twelve generations, for at least eighteen generations or for at least twenty-four generations. The method optionally provides for the steps of removing a portion of the virus-containing medium, contacting the portion with at least one substance which augments the activation of the virus for a sufficient amount of time for the activation to occur, then adding to the removed portion one or more compounds which inhibit or attenuate any of the cell toxic effects of the at least one or more substances for a sufficient amount of time for the inhibition or attenuation to occur, and then returning the portion to the cell culture. Suitable vertebrate cells for use with the invention include chicken embryo culture cells, VERO cells, CV-1 cells, LLC-MK2 cells, MDCK cells and MDBK cells, as well as vertebrate cell aggregates comprising a plurality of cell types.

In accordance with the objects of the invention, the virus is selected from the group of families consisting of orthomyxoviridae, paramyxoviridae and reoviridae and is preferably an Influenza virus. The substance that augments the activation of the virus is preferably a protease that cleaves a glycoprotein responsible for fusion of virus and host cell membrane such as the serine protease that cleaves Influenza hemagglutinin. Suitable serine proteases may be selected from the group consisting of the trypsin family and the family of subtilisin-like enzymes. More specifically, the serine protease may be selected the group consisting of trypsin, chymotrypsin, thermolysin, pronase, subtilisin A, elastase, pepsin, pancreatin, carboxypeptidase and furin.

In accordance with additional objects of the invention, the method includes the aspect wherein the substance which augments the activation is in a vessel or is immobilized on a carrier and wherein the Influenza virus has been altered to modify a cleavage site or to create a new cleavage site in the glycoprotein. When the method is applied to Influenza virus, the hemagglutinin of the Influenza virus is preferably altered to contain the cleavage site KKRKKR. In accordance with yet other objects of the invention, the compound that inhibits or attenuates any cell toxic effects of the activating substance is selected from the group consisting of soybean trypsin inhibitor, egg trypsin inhibitor and aprotinin and is preferably is provided in a vessel or immobilized on a carrier.

In accordance with still additional objects of the invention, the method provides further for monitoring the growth, infection and activation levels of the culture, for varying the conditions of the culture to maximize growth, infection and activation levels, for harvesting the virus from the culture, and for preparing a vaccine with the harvested virus. The method of the invention provides further for the treatment of Influenza virus infection or for the prevention of Influenza virus infection by administering to an animal a vaccine obtained by the methods described herein.

In accordance with other objects of the invention, a method is provided for augmenting or optimizing the production of viruses comprising the steps of providing a cell culture of vertebrate cells, growing the cells in serum-free medium, infecting the cell culture with a virus, incubating the cell culture infected with the virus to propagate the virus into the medium to produce a virus-containing medium, removing a portion of the virus-containing medium, contacting the portion with at least one substance which augments the activation of the virus, adding to the portion, at least one compound which inhibits or attenuates the cell toxic effects of the one or more substances that augment the activation of the virus, and returning the removed virus-containing medium portion to the cell culture and medium.

Further in accordance with the objects of the invention, the method provides that the steps of providing, growing, infecting and incubating optionally are performed in a first vessel and the steps of contacting and adding are performed in a second vessel and further that the first and second vessels are connected in a loop so that steps of providing, growing, infecting, incubating, removing, contacting, adding and returning can be performed in a closed cycle or the like. Other options within the scope of the invention include the steps of providing, growing, infecting and incubating are performed in a first vessel, the step of contacting is performed in a second vessel, and the step of adding is performed in a third vessel and, optionally, wherein the first vessel, the second vessel and the third vessel are connected in a loop so that all of the steps can be performed in a batchwise manner, cyclic manner or the like.

In accordance with additional objects of the invention, the vertebrate cells of the method may comprise a plurality of cell types or those chosen from chicken embryo cell cultures, the VERO cells, CV-1 cells, LLC-MK2 cells, MDCK cells and MDBK cells. In one preferred form of the invention, the virus may be an Influenza virus and the substance to activate the virus is a protease that cleaves Influenza hemagglutinin, such as one or more serine proteases selected from the trypsin family or the family of subtilisin-like enzymes selected from the group of trypsin, chymotrypsin, thermolysin, pronase, subtilisin A, elastase, pepsin, pancreatin, carboxypeptidase and furin.

In accordance with still other objects of the invention, the virus can be altered to modify an activation site, such as a protein cleavage site, or to create a new cleavage site in the protein, for example in Influenza virus hemagglutinin a preferable modification according to the invention is to insert the cleavage site KKRKKR (SEQ ID No:4). The method of the invention also provides that the one or more compounds which inhibit or attenuate the cell toxic effects of the one or more proteases or one or more substances that augment the activation of the virus, are one or more selected from the group consisting of soybean trypsin inhibitor, egg trypsin inhibitor or aprotinin, and further that the compounds may be in a vessel, pipe, manifold, coil or other container or immobilized on a carrier which in turn may be a container or the like.

In accordance with yet additional objects of the invention, the methods provide for the monitoring the growth, infection and activation levels of the culture, and as well as for varying the conditions of the culture to maximize the growth, infection and activation levels of the cells and virus, and for harvesting the virus from the culture, preparing a vaccine with the harvested virus, and for the treatment of Influenza virus infection and for the prevention of Influenza virus infection by administering to an animal a vaccine obtained by the method.

In accordance with yet other objects of the invention, there is provided a method for optimizing the production of one or more products of cultured cells, comprising the steps of providing cells in culture in a first vessel, transferring a portion of the cells to a second vessel, activating the portion of the cells in the second vessel by the addition of one or more exogenous substances to optimize the production of a desired product, transferring the portion of the cells to a third vessel, adding compounds to the portion of the cells in the third vessel which attenuate the cell toxic effects of the one or more exogenous substances, wherein the first, second and third vessels are connected in a circular loop system or the like, returning the portion of the cells to the first vessel. The method provides also for batchwise or continuous production, for effecting processing of a portion of the culture can include substantially all of the cells in the culture, and for culturing the cells and virus in a culture medium that provides optimum conditions for cellular growth and production.

In accordance with still additional objects of the invention, a method is provided for increasing the infectivity of viruses that express a protein involved in activation of the virus, comprising the steps of providing a culture of vertebrate cells, growing the cells in serum-free medium, infecting the culture with a virus that has a modified cleavage site in the protein involved in activation of the virus, wherein the modified cleavage site increases the susceptibility of the virus to the cleavage enzymes in a culture of vertebrate cells, and incubating the cell culture infected with the virus to propagate the virus and to produce virus-containing medium. The method is particularly useful wherein the virus is an Influenza virus that has been altered to modify a cleavage site in its hemagglutinin or to create a new cleavage site, preferably KKRKKR (SEQ ID No:4) or the like, in its hemagglutinin, and wherein the vertebrate cells are chosen from chicken embryo culture cells, VERO cells, CV-1 cells, LLC-MK2 cells, MDCK cells and MDBK cells as well as vertebrate cell aggregates comprising a plurality of cell types.

The aspect of the invention pertaining to increasing the infectivity of a virus also may comprise the steps of removing a portion of the medium containing the virus, contacting the portion with at least one substance which augments the activation of the virus, adding to the virus-containing portion at least one compound which inhibits or attenuates the cell toxic effects of the one or more substances that augment the activation of the virus, and returning the removed portion to the cell culture and medium. Preferred substances which augment the activation of the virus are proteases which activate a protein involved in virus activation, for example those which cleave Influenza hemagglutinin which include the serine proteases selected from the trypsin family or the family of subtilisin-like enzymes, preferably selected from the group of trypsin, chymotrypsin, thermolysin, pronase, subtilisin A, elastase, pepsin, pancreatin, carboxypeptidase, and furin.

Further in accordance with the objects of the invention, another aspect of the method pertains to increasing the infectivity of a virus may include, after the cells are grown in serum-free medium, and before the culture is infected with a virus, the vertebrate cells are grown in the serum-free medium for at least six generations, for at least twelve generations, for at least eighteen generations or for at least twenty-four generations. The aspects of the invention pertaining to increasing the infectivity of a virus may have the steps performed in a continuous process or in a batchwise manner or the like, and that the one or more compounds which inhibit or attenuate the cell toxic effects of the one or more proteases or one or more substances that augment the activation of the virus, are one or more chosen from the group consisting of soybean trypsin inhibitor, egg trypsin inhibitor or aprotinin, and further that the compounds may be in a vessel, pipe, manifold, coil or other container or immobilized on a carrier, which in turn may be in a container or the like.

In accordance with yet additional objects, relating to another aspect of the invention pertaining to increasing the infectivity of a virus may include the monitoring of the growth, infection and activation levels of the culture, as well as for varying the conditions of the culture to maximize the growth, infection and activation levels of the cells and virus, and for harvesting the virus from the culture, preparing a vaccine with the harvested virus, and for the treatment of Influenza virus infection and for the prevention of Influenza virus infection by administering to a mammal a vaccine obtained by the method.

DETAILED DESCRIPTION OF THE PREFERRED EMBODIMENTS

The present invention is a vast improvement over the prior art. The present invention is based on a system using vertebrate cell aggregates or vertebrate cells that have been adapted to serum-free growth conditions to grow a desired virus. The method provided by the present invention comprises the periodic or continuous removal of "treatment portions" of the virus-containing culture medium from the culture vessel into an "augmentation loop" and the subsequent return of the treatment portions to the culture vessel. In the augmentation loop, the treatment portion is subjected to exposure to one or more substances which increase the infectivity of the virus. The term "substances" refers to proteases of natural or synthetic origin, including homologs, analogs, muteins, mimetics, pro-enzymes and fragments of proteases. Other compounds which can effect activation, typically by proteolytic cleavage, are also within the scope of the present invention and are thus "substances". For example, high concentrations of proteases that augment the activation of the virus, such as trypsin or subtilisin A, can be introduced into the treatment portion. The proteases can be then neutralized, inhibited or removed and the treatment portion returned to the culture vessel. Thus, the positive effects of the proteases on the virus are realized while the negative effects of the proteases on the culture are reduced or eliminated. As one consequence, the method of the present invention allows high yield production of virus that can be readily scaled up to large scale production rates. Until now, methods that employed proteases for viral activation were not applicable for the large scale production of virus, since the removal of proteases by repeated washes is virtually impossible to perform with large fermentors.

The present method adapts some of the aspects of chicken embryonic cell ("CEC") aggregates to other cell culture lines. CEC aggregates have been described for the propagation of viruses, such as TBE virus. CEC culture systems are composed of cell aggregates having a diameter in a range of between about 100 μm to 1000 μm. These cell aggregates are derived from the entire chicken embryo without removal of brain and inner organs. Because of the wide range of cell types available and the consequent supply of a number of different classes of cellular proteases, activation of a broad range of Influenza viruses is possible. If a particular strain cannot be activated in the system of the present invention by endogenous enzymes, activation can be achieved by addition of extraneous proteases such as trypsin or subtilisin.

In addition, the present system allows use of trypsin or other proteolytic enzymes at much higher concentrations than those normally tolerated by cells in culture, thereby increasing the level of viral activation, for example the cleavage of HA, while eliminating substantially the toxic effects of trypsin on the cells. This advantageous aspect is achieved by use of a system, whereby a portion of virus-containing medium from a cell fermentation vessel is removed to a second location such as a column, tube, pipe, manifold, reaction flask or other type of second vessel, and contacted therein with trypsin or other proteases or substances which augment the activation of the virus. After an incubation period sufficient to activate the virus, the removed portion is transferred to a third location such as a column, tube, pipe, manifold, reaction flask or other type of second vessel and contacted therein with trypsin inhibitor or compounds which inhibit or attenuate the cell toxic effects of the proteases or substances that augment the activation of the virus. After an incubation period sufficient to inhibit or attenuate the cell toxic effects of the proteases or substances that augment the activation of the virus, the removed portion is returned to the cell fermentation vessel.

The present invention also includes the aspect of altering the susceptibility of a virus strain to trypsin or other proteolytic enzymes in order to ensure the efficient production of new virus strains which cannot be activated by standard methodologies. The specific concepts underlying the claimed invention have not been recognized prior to the present invention.

In the augmentation loop aspect of the present invention, high concentrations of trypsin or other exogenous enzymes can indeed be utilized to augment virus activation in serum-free vertebrate cell lines as well as in CEC cultures. Specifically, following incubation of media containing infected cells and virus, the trypsin or other enzymes are neutralized or removed at intervals by trypsin inhibitors or by inhibitors for the enzyme used such as immobilized antibodies which can bind to a protease. This aspect of the invention allows a higher degree of activation compared to other methods which employ lower concentrations of trypsin and, because the present method provides that the trypsin is neutralized or removed at regular intervals, allows continuous production and harvesting of the virus rather than batch production and a single harvest. Most importantly, the present invention provides a method that can easily be scaled up to large scale fermentation for the high yield production of Influenza and other viruses.

To allow the high yield production of all types of viruses, including all strains of Influenza virus, the present invention provides a method for efficient virus production in vertebrate cells. Being primarily designed for the high yield production of Influenza virus, the method of the present invention can be used for the high yield production of any virus that requires substances, such as proteases, that are harmful to cellular hosts.

Examples of viruses that require an activation step are those of the orthomyxoviridae family, such as Influenza viruses A, B and C, those of the paramyxoviridae family, such as parainfluenza virus Types 1, 2, 3 and 4 or Newcastle Disease virus, and those of the reoviridae family, for example, rotavirus Types A, B and C. Activation of these viruses involves proteolysis.

One aspect of the invention with respect to the vertebrate cells is that they are adapted to serum-free growth conditions for multiple generations, preferably for at least six cell generations, more preferably for at least twelve cell generations, even more preferably for at least eighteen cell generations, and still more preferably for at least twenty-four cell generations before infection with the virus. The use of vertebrate cells that have been adapted to serum-free growth conditions is not described in the prior art. Because of the present invention, the production of Influenza virus in cell lines like VERO and LLC-MK2 is possible. Moreover, the invention increases production rates of virus in CV-1 cells.

For further augmentation of virus production levels, the inventors provide the optional method of treating the virus producing cell culture with one or more substances, that cleave Influenza hemagglutinin thereby rendering the newly produced virus infectious.

Another embodiment of the method for high yield production of Influenza virus refers to the use of CEC aggregates. Such cell aggregates comprise a plurality of cell types that include many different endogenous proteases. If the endogenous proteases of the system are not enough to efficiently activate Influenza virus, activation can be achieved by addition of extraneous substances, such as proteases and the like.

In accordance with one aspect of the invention, the cleavage of Influenza hemagglutinin by a protease is physically separated from the primary cultivation of the host cells and the infection of the host cells by the virus. This allows much higher protease concentrations than described in the prior art. In the prior art where the protease was part of the medium in the primary culture, protease concentrations had to be kept low to minimize the toxic effects on cellular processes and host cell growth rates. As a result, the activation of Influenza virus by proteolytic cleavage of hemagglutinin was not complete and non-infectious virus particles were maintained in the culture. Prior art approaches to deal with this problem involve growing Influenza virus in embryonated chicken eggs. This technique, however, has many disadvantages as there are many labor intense steps which are susceptible to contamination.

According to the invention, following incubation of host cells with virus for a time span allowing at least one round of virus replication, one or more proteases are added. According to one aspect of the invention, protease activation of virus occurs in a location removed from the primary culture vessel, by employing an "activation vessel" which can be a column, pipe, tube, coil, or other container which facilitates contacting the virus with the activating protease, while eliminating or minimizing the cell toxic effects of the protease. Accordingly, a new and inventive method is provided that allows the use of proteases, such as trypsin, at much higher concentrations than those normally tolerated by culture cells to thereby further increase the level of viral activation, such as Influenza HA cleavage.

Following incubation of medium containing infected cells, virus and one or more proteases in the activation vessel of the loop, the proteases are inactivated or removed by protease inhibitors or the like. According to one aspect of the invention, this neutralization step occurs in a location which is separate from both the primary culture vessel and the activation vessel.

After efficient inactivation of the proteases, the activated viruses can be recycled back into the cultivation process without a negative interference of the proteases with the growth of the host cells. Because of these aspects, the present invention provides an advantageous and efficient method for the continuous production and harvesting of viruses.

The present invention also comprises the advantageous aspect of altering the susceptibility of a virus strain to a protease, such as trypsin, in the event that a strain should arise which cannot be activated by other methodologies. In the case of Influenza, there are several structural properties of the HA that determine the differential cleavability, but the key factor is the amino acid sequence at the cleavage site. It has been demonstrated that susceptibility of hemagglutinin to cleavage is not a fixed characteristic of the molecule. The present invention provides advantageously for the alteration of hemagglutinin to ensure its susceptibility to cleavage by available proteases.

Specifically, hemagglutinin can be altered to adapt subject virus to a novel host cell. Cleavability of the hemagglutinin of the adapted virus in a new host cell type can sometimes be obtained by a single amino acid substitution close to the cleavage site. Thus, alterations in the cleavability of the HA of a particular virus strain can be generated by known site-directed mutagenesis and PCR techniques. By employing these techniques in the present invention, virtually any Influenza virus strain can be modified to be susceptible to enzyme activation. This can be done while maintaining the native immune profile of the hemagglutinin. Thus, the methodology of the present invention allows the large scale production of all types of Influenza virus to a high titre.

In accordance with one aspect of the invention, the Influenza virus is modified to create a modified, and preferably more efficient, cleavage site in the hemagglutinin. Such a modulated cleavage site is preferably KKRKKR (SEQ ID NO:4) or the like, that is, lysine, lysine, arginine, lysine, lysine, arginine, which are basic amino acids. The modulated cleavage site is designed according to the invention to replace the naturally occurring hemagglutinin cleavage site of any type of Influenza virus. The preferred (or "master") cleavage site KKRKKR (SEQ ID NO:4), was designed according to the consensus sequence for protease recognition, R-X-K/R-R as described by Vey et al., "Hemagglutinin Activation of Pathogenic Avian Influenza Viruses of Serotype H7 Requires the Protease Recognition Motif R-X-K/R-R", Virology, 188:408–413 (1992).

Until the present invention, it was only possible to grow high yields of Influenza virus when the virus strains themselves provided an efficient cleavage site. The modification of the hemagglutinin cleavage site as it is provided by the present invention enables the growth in vertebrate cell culture of any type of Influenza virus to high yield. As a consequence, vaccines can be prepared that are effective against all Influenza strains present in a given population at a certain time.

According to one aspect of the invention, high yield production of Influenza virus is accomplished by an increase in the level of HA-activation, that is, activation of the virus, and the use of an augmentation loop system, whereby virus containing medium from a cell fermentor containing cells cultured and infected according to the present invention is continually removed to a vessel containing one or more proteases, such as trypsin. After a certain incubation time, the medium is transferred to a vessel containing a substance which inhibits or removes the protease activity, and, finally, the medium is subsequently returned to the cell-containing fermentor.

In summary, the method of producing Influenza virus as provided by the present invention is characterized by highly advantageous features. The present method, inter alia, allows the high yield production of Influenza virus, allows the use of concentrations of proteases much higher than in previous methods, and, consequently, the efficient activation of viruses, including all strains of Influenza virus. Moreover, due to the flexibility of the present method, its augmentation loop aspect allows the ready adaptation of production conditions to any serotype of Influenza and other viruses.

An additional advantage of the invention is found in its aspects which relate to the modification of the cleavage site of a protein involved in activation, such as Influenza hemagglutinin, to thereby permit substantial increases in the yield of viruses that with conventional methods can be cultivated at low yield only. Further advantages of the presently claimed method relate to its resultant production of Influenza virus which is substantially free of egg proteins. Moreover, the method of the present invention is capable of automation, requires little manual labor when compared with conventional culture techniques and is less susceptible to contamination because of its fewer process steps.

In addition, the present method produces a much higher virus titre when compared with other cell culture methods. Also, the present invention provides a method which enables the growth of all human Influenza virus strains tested to levels approaching that obtained in the embryonated egg without the disadvantages of using the embryonated egg. Finally, the method allows upscaling of the virus production to fermentors with volumes on the order of 100–1000 liters, thereby permitting the attainment of high production efficiencies.

The augmentation loop aspect of the present invention is adaptable to the production of any type of virus and any type of cellular product. The augmentation loop system of the present invention allows the independent optimization of parameters of cell growth and synthesis rates. Therefore, the augmentation loop system can be used in all cases where efficient synthesis rates of a virus or another cellular product, for example, a recombinant protein, require an activation step that otherwise would be toxic or harmful to cellular processes of the primary culture.

Due to the physical separation of fermentation, activation, and inactivation steps, the activation and inactivation steps can occur under chemical or physical conditions that otherwise would not be tolerate by cells in a conventional cell culture system. As a consequence, the activation steps of the present invention are more efficient and highly increase production rates. Conditions that are not tolerated by cells in a conventional cell culture system can be of chemical or physical nature, that is, substances that are required at concentration that are harmful to cells as well as physical conditions such as temperatures or pressures that are harmful to cells when exhibited for a certain time span.

A "circular" or "loop" fermentor system consisting of three or more connected vessels, that is, a cultivation vessel, an activation vessel, and an inactivation vessel, combine to form a preferred general system for practicing the present invention. Within the context of the invention, a "vessel" can be a fermentor, tube, pipe, column, manifold or any type of containment device that is suitable for carrying out the desired step. For example, a cultivation vessel might be a conventional large-scale fermentation container while an activation vessel might be a column having immobilized trypsin therein. Similarly, an inactivation vessel might be a manifold having therein a substance which inactivates any trypsin which escapes from the activation vessel to thereby prevent the deleterious effects of trypsin from being cycled to the primary cultivation vessel.

The advantages of the present invention are illustrated in the following examples. The examples are illustrative of the invention but do not limit its scope. In the examples and tables below, B/Massachusetts refers to B/Massachusetts/71; B/Panama refers to B/Panama/45/90; B/Yamagata refers to B/Yamagata/16/88; Brazil refers to A/Brazil/11/78 (H1N1); California refers to A/California/10/78 (H1N1); Singapore 6 refers to A/Singapore/6/86 (H1N1); Taiwan refers to A/Taiwan/1/86 (H1N1); Texas 36 refers to A/Texas/36/91 (H1N1); USSR refers to A/USSR/90/77 (H1N1); A2 Singapore refers to A/Singapore/1/57 (H2N2); Beijing refers to A/Beijing/353/89 (H3N2); Guizho refers to A/Guizho/54/89 (H3N2); Hongkong refers to A/Hongkong/1/68 (H3N2); Hongkong 5 refers to A/Hongkong/5/83 (H3N2); Shanghai 16 refers to A/Shanghai/16/89 (H3N2); Texas refers to A/Texas/1/77 (H3N2); and Victoria refers to A/Victoria/3/75 (H3N2).

EXAMPLE 1

Hemagglutinin titre obtained from various Influenza strains produced by embryonated eggs and spinner culture with or without proteases Influenza strains listed in Table 1 were used either for infection of embryonated chicken eggs or the CEC spinner culture.

The CEC-spinner culture aggregates were produced as disclosed in PCT published application WO 91/09937. Two embryonated eggs are required to generate 100 ml of biomass culture. 100 ml CEC spinner culture were infected with 1 ml of Influenza virus containing allantoic fluid. Addition of the protease was immediately carried out after infection. Either Trypsin (Seromed) or Subtilisin A (Fa. Novo) were added to the medium to a concentration of 20 mU/ml and 30 μg/ml, respectively. The CEC spinner culture was incubated for 3–4 days with removal of the half of the medium volume (50 ml) every day. Fresh medium with or without protease was added to an end volume of 100 ml culture. After 4 days of incubation and daily harvesting of virus-containing medium, the pooled cell culture medium was collected and the HA-titre was determined. The HA-titre was determined as described by Hirst, "The Agglutination of Red Cells by Allantoic Fluid of Chick Embryos Infected with Influenza Virus", *Science*, 94:22–23 (1941) and Barrett et al., "Viruses" in Methods of Immunological Analysis, Masseyeff R. F., Albert W. H., and Staines N. A. (eds), Vol. 2, V. C. H. Weinheim, 116–132 (1993).

10–11 day old embryonated eggs were infected with 200 μl virus containing allantoic fluid per egg. Infected eggs were incubated for 2–3 days at 37° C. as described by Burnett, "Influenza Virus Infections of the Chick Embryo by the Amniotic Route", *Austral. J. Exp. Biol. Med. Sci.*, 18: 353–360 (1940). The egg was opened and the HA titre was determined as already described.

Table 1 compares the hemagglutinin titre obtained from various Influenza strains produced by embryonated eggs and spinner culture with or without proteases. The data show that the use of the CEC spinner culture and the addition of protease according to the present invention increases the yield of the most strains to a level approaching the yields of virus strains grown in the embryonated egg cultures, all without the disadvantages inherent in other culture methods.

TABLE 1

Maximum HA-Titre obtained for different Influenza strains in embryonated eggs and in CEC-spinner-cultures with and without the proteases Trypsin and Subtilisin A

| | | | HA-Titre | | | |
|---|---|---|---|---|---|---|
| | | Vaccine | CEC spinner culture/Protease | | | Egg |
| Subtype | Strain | Year | none | Trypsin | Subtilisin A | |
| B | B/Massachusetts | | 7 | 8 | n.d. | 9 |
| | B/Panama | 1991/92, 92/93 | 6 | 4 | 5 | 8 |
| | B/Yamagata | 1990/91, 91/92, 92/93 | 3 | 5 | 5 | 8 |

TABLE 1-continued Maximum HA-Titre obtained for different
Influenza strains in embryonated eggs and in
CEC-spinner-cultures with and without the
proteases Trypsin and Subtilisin A

| | | | HA-Titre | | | |
|---|---|---|---|---|---|---|
| | | Vaccine | CEC spinner culture/Protease | | | Eg |
| Subtype | Strain | Year | none | Trypsin | Subtilisin A | g |
| A/H1N1 | Brazil | | 7 | 1 | n.d. | 10 |
| | California | | 2 | 2 | 6 | 8 |
| | USSR | | 7 | 2 | n.d. | 10 |
| | Singapore 6 | 1990/91, 91/92, 92/93 | 2 | 4 | 4 | 7 |
| | Taiwan | 1991/92 | 4 | 6 | 4 | 9 |
| | Texas 36 | 1992/93 | 5 | 4 | n.d. | 6 |
| A/H2N2 | A2 Singapore | | 2 | 7 | n.d. | 9 |
| A/H3N2 | Hong Kong | | 2 | 8 | 6 | 10 |
| | Hong Kong 5 | | 2 | 7 | 6 | 8 |
| | Texas | | 2 | 6 | n.d. | 8 |
| | Victoria | | 2 | 6 | n.d. | 8 |
| | Guizho | 1990/91 | 2 | 6 | 5 | 6 |
| | Shanghai 16 | 1990/91 | 2 | 6 | 6 | 6 |
| | Beijing | 1991/92, 92/93 | 2 | 6 | 6 | 8 | n.d. = not done

EXAMPLE 2

Virus yield obtained from various Influenza strains produced by embryonated eggs and CEC biomass culture Embryonated eggs and biomass CEC spinner culture were infected with various strains of Influenza virus as listed in Table 2 and described in Example 1.

The embryonated egg yields a maximum of 7 ml allantoic fluid, which is harvested 72 hours after inoculation. Two embryonated eggs are required to produce 100 ml of biomass culture. By harvesting half of the culture volume after 48 and 72 hours and the total volume after 96 hours, 200 ml of virus containing medium were collected over a 96 hour period. The biomass culture provided 100 ml virus antigen per egg compared to a maximum of 7 ml from the inoculated egg, which is a 14-fold increase in volume. When this factor is taken into account, the present method produces a higher virus antigen yield when compared with the embryonated egg method. This is illustrated by the calculations in Table 2.

Table 2 compares the virus yield obtained from various Influenza strains produced by embryonated eggs and by those produced by the present invention. The HA-titre was calculated as already described for 100 ml of biomass spinner culture medium obtained from one egg and 7 ml of allantoic fluid per egg. Thus, the data in Table 2 present the total virus yield per egg in CEC spinner culture obtained with or without proteases, calculated from the results of Example 1. Dependent on the Influenza strain used, the biomass spinner culture method results in an approximately 2-14 fold increase in virus antigen compared to the yield obtained in the embryonated egg. Incubation of the infected biomass spinner culture without the addition of a protease reached a virus yield close to that obtained in eggs for B-Panama, Brazil, USSR and Texas 36, which could not be increased by the protease. The virus yield of all other Influenza virus strains was increased by the addition of a protease. Thus, insufficient endogenous protease content of the biomass cell culture can be overcome by the exogenous addition of a protease to activate the viral hemagglutinin.

TABLE 2

Comparison of Virus Yield in Embryonated Egg
and Biomass Culture Total Yield/Egg

| | | | Biomass Culture | Egg | Ratio Biomass |
|---|---|---|---|---|---|
| Subtype | Strain | Protease | HA Units × 100 ml | HA Units × 7 ml | Culture/ Egg |
| B | B/Mass. | T | 25600 | 3584 | 7.1 |
| | B/Panama | N | 6400 | 1792 | 3.6 |
| | B/Yamagata | T | 3200 | 1792 | 1.8 |
| A/H1N1 | Brazil | N | 12800 | 7168 | 1.8 |
| | California | S | 6400 | 1792 | 3.6 |
| | USSR | N | 12800 | 7168 | 1.8 |
| | Singapore 6 | T | 1600 | 896 | 1.8 |
| | Taiwan | T | 6400 | 3584 | 1.8 |
| | Texas 36 | N | 3200 | 448 | 7.1 |
| A/H2N2 | A2 Singapore | T | 12800 | 3584 | 3.6 |
| A/H3N2 | Hong Kong | T | 25600 | 7168 | 3.6 |
| | Hong Kong 5 | T | 12800 | 1792 | 7.1 |
| | Texas | T | 6400 | 1792 | 3.6 |
| | Victoria | T | 6400 | 1792 | 3.6 |
| | Guizho | T | 6400 | 448 | 14.3 |
| | Shanghai 16 | T | 6400 | 448 | 14.3 |
| | Beijing | T | 6400 | 1792 | 3.6 |

N: none
T: Trypsin
S: Subtilisin A

EXAMPLE 3

Large scale-up of Influenza virus production in CEC fermentor cultures

A scale-up of the 100 ml spinner culture to an automated 2 liter fermentor was performed. A 2 liter fermentor of biomass cell culture was inoculated with 2 ml Influenza virus containing allantoic fluid with an HA titre of 6-8 with continuous medium changes at 37° C.

The method of the invention using large scale fermentor culture employs trypsin activation in an augmentation loop system, whereby portions of the media containing the desired virus are continuously removed from the fermentor to a vessel containing trypsin or any other required protease. In the vessel containing trypsin or subtilisin A with a concentration of 20 mU/ml and 30 µg/ml, respectively, the virus is activated over a period of approximately one hour. The medium containing the trypsin activated virus is then pumped into a vessel containing soya bean trypsin inhibitor (Sigma) for about 1 h with a concentration sufficient to neutralize the residual trypsin activity. The medium containing neutralized trypsin with virus is then returned to the fermentor for a further cycle of replication. By continuous removal of the biomass cell culture medium from the fermentor and addition of fresh culture medium, 4–5 l of virus-containing medium was obtained during a time period of 96 hours. The method of the invention allows activation of virus with much higher concentration of trypsin than would be possible with conventional methods, where high concentrations of the protease would have detrimental effects on the cell culture and virus if incubated with them over a prolonged period.

Table 3 shows the advantages of the method as applied to the virus strain California, which can be activated by trypsin using the augmenter loop system and later employing a trypsin inhibitor.

TABLE 3

Maximum HA-Titre obtained for different Influenza strains in 100 ml CEC-spinner cultures and 2 liter CEC-fermentor cultures

| | | | HA - Titre | | | |
|---|---|---|---|---|---|---|
| | | Vaccine | | CEC culture | | |
| Subtype | Strain | Year | Protease | spinner | fermentor | Egg |
| B | B/Panama | 91/92, 92/93 | N | 6 | 6 | 8 |
| A/H1N1 | Brazil | | N | 7 | 7 | 10 |
| | California | | S | 6 | 6 | 8 |
| | | | T | 2 | 6 | |
| | Singapore 6 | 90/91, 91/92, 92/93 | S | 4 | 4 | 7 |
| | | | T | 4 | 4 | |
| A/H3N2 | Hongkong 5 | | S | 6 | 6 | 8 |
| | | | T | 7 | 7 | |
| | Beijing | 91/92, 92/93 | S | 6 | 7 | 8 |
| | | | T | 6 | 7 | |

N: none
S: Subtilisin A
T: Trypsin

EXAMPLE 4

Comparison of HA titre of Influenza virus in MDCK cell culture, standard CEC culture and CEC biomass aggregates Embryonated eggs, CEC fermentor culture, CEC and MDCK monolayer cultures were infected with Influenza virus strains as listed in Table 4. Infection of embryonated eggs were performed as described in Example 1 and with the fermentor culture as described in Example 3. Primary chicken embryo cells were propagated as described by Mayr et al., "Vergleichende Studien über die Züchtung von Gelfl ügel-pockenviren in der Zellkultur", Arch. ges. Virusforsch., 10:72–102 (1961) and infected with Influenza virus containing allantoic fluid with a HA titre of 6–8 units.

Continuous cell lines of MDCK cells were propagated as monolayers and infected with Influenza virus containing allantoic fluid with a HA titre of 6–8 units. Incubation was carried out until development of maximum cytopathic effect (cpe) or for a maximum of 72 h and HA-titre was determined as previously described.

These data demonstrate that the method of invention produces higher yields for all viruses studied in the CEC fermentor culture than in CEC monolayer culture or other cell culture methods. Table 4 compares the HA titre obtained for different strains of Influenza A and a B strain in MDCK cell culture, standard CEC culture and CEC biomass aggregates in the presence and absence of trypsin and subtilisin A. Slightly higher titres can be obtained in MDCK cultures, but these cells are not licensed for human vaccine production. Activation of California, Singapore 6, Hongkong, Hongkong 5 and Beijing by trypsin or subtilisin leads to titres higher than those obtained with or without activation in standard CEC cultures or in MDCK culture.

TABLE 4

Comparison of HA titres of Various Influenza Strains in CEC Biomass Cultures, CEC Monolayer Cultures and MDCK Monolayer Cultures with and without addition of Proteases with titres in embryonated eggs

| | | | HA-Titre | | | | | | |
|---|---|---|---|---|---|---|---|---|---|
| | | | | | | Tissue culture "monolayer"/Protease | | | |
| | | Vaccine | CEC fermentor - culture | | | CEC | | MDCK | |
| Subtype | Strain | Year | None | Trypsin | Subtilisin A | None | Trypsin | None | Trypsin | Egg |
| B | B/Panama | 91/91; 92/93 | 6 | 4 | 5 | 2 | 2 | 7 | 7 | 8 |
| A/H1N1 | Brazil | | 7 | 1 | n.d. | 5 | 5 | 8 | 8 | 10 |
| | California | | 2 | 6 | 6 | 2 | 2 | 5 | 5 | 8 |
| | Singapore 6 | 90/91; 91/92; 92/93 | 2 | 4 | 4 | 0 | 0 | 3 | 2 | 7 |
| A/H3N2 | Hongkong | | 2 | 8 | 6 | 2 | 5 | 6 | 6 | 10 |

TABLE 4-continued

Comparison of HA titres of Various Influenza Strains in CEC Biomass Cultures, CEC Monolayer Cultures and MDCK Monolayer Cultures with and without addition of Proteases with titres in embryonated eggs

| | | | HA-Titre | | | | | | |
|---|---|---|---|---|---|---|---|---|---|
| | | | | | | Tissue culture "monolayer"/Protease | | | |
| | | Vaccine | CEC fermentor - culture | | | CEC | | MDCK | |
| Subtype | Strain | Year | None | Trypsin | Subtilisin A | None | Trypsin | None | Trypsin | Egg |
| | Hongkong 5 | | 2 | 7 | 6 | 0 | 0 | 4 | 5 | 8 |
| | Beijing | 91/92; 92193 | 2 | 7 | 7 | 2 | 2 | 5 | 6 | 8 | n.d. = not done

EXAMPLE 5
Antibody Response after Immunization with Influenza Virus Vaccine

The Influenza A H1N1 strain Brazil was grown in embryonated eggs as previously described and the allantoic fluids were harvested, pooled and frozen at −20° C. The same strain was also grown in CEC biomass fermentor culture as described previously. The tissue culture medium supernatant was concentrated by ultrafiltration using a 100,000 M.W. cut-off filter and this material and the allantoic fluid from embryonated cells were purified by ultracentrifugation over a 20% sucrose cushion. The virus pellets were resuspended in buffer and inactivated by U.V./psoralene treatment (10 µg/ml 4-aminoethyltrioxalen Hydrochloride, U.V. intensity of 20 mW/cm$^2$) for 15 minutes. The antigen preparations were then diluted to give a concentration of 20 µg/ml and adjuvanted with Al(OH)$_3$.

Groups of ten mice were then immunized with a dose of 10 µg antigen and boostered with the same dose four weeks later. Two weeks after the booster injection, the animals were sacrificed and serum HAI titre and ELISA titre was determined as shown in Table 5.

These data demonstrate that there was no significant difference in the HAI and ELISA antibody titres generated by immunization with the Brazil strain grown by standard egg technology or by the claimed method of this invention.

TABLE 5

Comparison of Antibody Response in Mice (Pool of 10 immunized mice each) After Immunization with Vaccines Produced in Embryonated Eggs and Mice Immunized with Vaccines Produced in a CEC Biomass Fermentor

| | | Embryonated Egg | | | Fermentor | |
|---|---|---|---|---|---|---|
| | | Antibody Titre | | | Antibody Titre | |
| Subtype | Strain | HAI | ELISA | Protease | HAI | ELISA |
| A/H1N1 | Brazil | 2560 | 102400 | — | 2560 | 102400 |
| | California | 2560 | 51200 | S | 5120 | 102400 |
| A/H3N2 | Hong Kong 5 | 2560 | 204800 | T | 2560 | 102400 |
| B | B/Panama | 160 | 102400 | — | 160 | 102400 |

—: none
T: Trypsin
S: Subtilisin A

EXAMPLE 6
Comparison of HA titres of different Influenza strains in VERO monolayer cultures in conventional medium containing fetal calf serum and in serum-free medium in the presence and absence of trypsin Conventional VERO cells and serum-free VERO cells were infected with Influenza virus strains as listed in Table 6. Continuous cell lines of VERO cells were propagated as monolayers in either conventional DMEM medium (Dulbecco's Eagle Medium) containing 5% fetal calf serum (FCS) or in serum-free DMEM medium (PCT Application WO 91/09935). Cells were infected with Influenza virus containing allantoic fluid with a HA titre of 6–8 units. Incubation was carried out until development of maximum cytopathic effect or for a maximum of 72 hours and HA titres were determined as described previously. After infection, media contained either no trypsin or 0.002% trypsin (Seromed). The data summarized in Table 6 demonstrate that the addition of trypsin to a medium containing 5% FCS for some virus strains allows low yield virus production. Significantly, the use of serum-free medium plus trypsin, however, gives high yield production for all virus strains tested.

TABLE 6

Maximum HA-titres obtained for different Influenza strains in conventional VERO monolayer cultures and in serum-free VERO monolayer cultures with and without trypsin.

| | | | Conventional VERO "monolayer" | | serum-free VERO "monolayer" | |
|---|---|---|---|---|---|---|
| Subtype | Strain | Vaccine Year | −trypsin | +trypsin | −trypsin | +trypsin |
| A/H1N1 | Brazil | | 0 | 3 | 5 | 8 |
| | California | | 0 | 0 | 0 | 6 |
| A/H3N2 | Hongkong | | 0 | 3 | 0 | 6 |
| | Hongkong 5 | | 0 | 3 | 0 | 7 |
| | Beijing | 91/92; 92/93 | 0 | 0 | 2 | 8 |

EXAMPLE 7
Comparison of HA titres obtained for different Influenza strains in embryonated eggs, serum-free VERO monolayer cultures and in serum-free VERO fermentor cultures in the presence and absence of trypsin Embryonated eggs, serum-free VERO monolayer cultures and serum-free VERO fermentor cultures were infected with Influenza virus strains as listed in Table 7. Infection of embryonated eggs was performed as described in Example 1 and of fermentor culture as described in Example 3. Continuous cell lines of serum-free VERO cells were propagated as monolayers and infected with Influenza virus containing allantoic fluid with a HA-titre of 6–8 units. Incubation was carried out until development of maximum cytopathic effect (cpe) or for a maximum of 72 hours and HA-titre was determined as previously described.

The data were summarized in Table 7 demonstrate that the different virus strains grown in serum-free VERO cells approach the HA-titres of the virus strains grown in embryonated eggs.

TABLE 7

Maximum HA-titres obtained for different Influenza strains in embryonated eggs, in serum-free VERO monolayer cultures and in serum-free VERO fermentor cultures with and without trypsin

| Subtype | Strain | Vaccine Year | HA-Titre −Trypsin Monolayer | HA-Titre −Trypsin Fermentor | HA-Titre +Trypsin Monolayer | HA-Titre +Trypsin Fermentor | Egg |
|---|---|---|---|---|---|---|---|
| B | B/Panama | 91/92, 92/93 93/94, 94/95 | 6 | 0 | 8 | 7 | 8 |
| A/H1N1 | Brazil | | 5 | 0 | 8 | 8 | 10 |
| | Singapore 6 | 90/91, 91/92 92/93, 93/94 94/95 | 3 | 0 | 6 | 6 | 7 |
| | Taiwan | 91/92 | 5 | n.d. | 6 | n.d. | 9 |
| A/H3N2 | Hongkong 5 | | 0 | 0 | 7 | 7 | 8 |
| | Beijing | 91/92, 92/93 | 2 | 0 | 8 | 8 | 8 |
| | Shang 16 | 90/91 | 2 | n.d. | 8 | n.d. | 6 |
| | Guizho | 90/91 | 2 | n.d. | 6 | n.d. | 6 |

EXAMPLE 8

Comparison of HA titres obtained from various Influenza strains in CV-1 and LLC-MK 2 cells cultivated in the presence of serum or under serum-free conditions.

CV-1 cells and LLC-MK 2 cells were grown as monolayers under serum-free conditions (SF) or under conventional conditions in the presence of 5% fetal calf serum (FCS) as indicated in the table. Cells were infected with Influenza virus containing allantoic fluid with a HA-titre of 6–8. Influenza virus strains were as indicated in the table. To demonstrate the effect of trypsin on HA-titres, all experiments were performed in the absence of trypsin or in the presence of 0.002% trypsin as indicated in Table 8. Experiments were performed as described in Example 6.

The data summarized in Table 8 demonstrate that for both cell lines, CV-1 and LLC-MK, maximum HA-titres are obtained under serum-free conditions and in the presence of trypsin.

TABLE 8

Maximum HA-titers obtained for Influenza strains in CV-1 and LLC-MK 2 cells cultivated in the presence of serum (PCS) or under serum-free conditions (SP)

| Cell-line | Serum | HA-Titre Brazil −trypsin | HA-Titre Brazil +trypsin | HA-Titre Beijing −trypsin | HA-Titre Beijing +trypsin | HA-Titre Hongkong 5 −trypsin | HA-Titre Hongkong 5 +trypsin |
|---|---|---|---|---|---|---|---|
| CV-1 | FCS | 3 | 5 | 2 | 3 | 0 | 0 |
| | SF | 6 | 7 | 7 | 7 | 5 | 8 |

TABLE 8-continued

Maximum HA-titers obtained for Influenza strains in CV-1 and LLC-MK 2 cells cultivated in the presence of serum (PCS) or under serum-free conditions (SP)

| Cell-line | Serum | HA-Titre Brazil −trypsin | HA-Titre Brazil +trypsin | HA-Titre Beijing −trypsin | HA-Titre Beijing +trypsin | HA-Titre Hongkong 5 −trypsin | HA-Titre Hongkong 5 +trypsin |
|---|---|---|---|---|---|---|---|
| LLC-MK2 | FCS | 0 | 0 | 0 | 0 | 0 | 0 |
| | SF | 2 | 7 | 2 | 7 | 0 | 6 |

EXAMPLE 9

Comparison of HA titres obtained from various Influenza strains in MDCK cells cultivated in the presence of serum or under serum-free conditions MDCK cells were grown as monolayers under serum-free conditions (SF) or under conventional conditions in the presence of 5% fetal calf serum (FCS) as indicated in Table 9. Cells were infected with Influenza virus containing allantoic fluid with a HA-titre of 6–8. Influenza virus strains were as indicated in Table 9. To demonstrate the effect of trypsin on HA-titres, all experiments were performed in the absence of trypsin or in the presence of 0.002% trypsin as indicated in Table 9. Experiments were performed as described in Example 6.

The data summarized in Table 9 demonstrate that, as in the case of CV-1 cells and LLC-MK 2 cells, maximum HA-titres are obtained under serum-free conditions and in the presence of trypsin.

TABLE 9

Maximum HA-titers obtained for Influenza strains in MDCK cells cultivated in the presence of serum (FKS) or under serum-free conditions (SF)

| | | HA-Titre | | | | | |
|---|---|---|---|---|---|---|---|
| | | Brazil | | Beijing | | Singapore 6 | |
| Cell-line | Serum | −Trypsin | +Trypsin | −Trypsin | +Trypsin | −Trypsin | +Trypsin |
| MDCK | FCS | 6 | 6 | 5 | 6 | 6 | 6 |
| | SF | 7 | 8 | 8 | 8 | 7 | 8 |

EXAMPLE 10
Alteration of the HA cleavage site of Influenza A/Hongkong/1/68 virus strain to the 'master cleavage site' KKRKKR Influenza A/Hongkong/1/68 was grown in embryonated chicken eggs, antibody-purified, lysed and viral RNA was prepared according to standard site-directed mutagenesis methodology (Enami et al., "Introduction of site-specific mutations into the genome of Influenza virus", Proc. Natl. Acad. Sci. USA, 87:3802–3805 (1990)). The viral RNA was subjected to reverse transcription and PCR employing primers complementary to the terminal non-coding, conserved regions of HA. Due to the conservation of this region, the 5'-primer (SEQ ID NO:1) 5'-ATGATGTCTAGAAGCAAAAGCAGGGGATAATTC-3' and the 3'-primer (SEQ ID NO:2) 5'-ATGATGCTGCAG-TTTAGTGAGGGTTAATAGTAGTAACAAGGGTGTTT-T-3' can be used for a wide range of Influenza virus strains. For further cloning, the 5'-primer carried a XbaI restriction site and the 3'-primer carried a PstI restriction site, additionally, the 3'-primer carried the T3-promoter sequence. After trimming of the restriction sites with the appropriate restriction enzymes (XbaI and PstI), the HA cDNA was subcloned into the XbaI and PstI sites of the multiple-cloning region of pUC19 (New England BioLabs) to obtain the pUC19-HA vector. Site-directed mutagenesis was performed as described by Palese et al. (WO 91/03552).

To mutate the HA cleavage site of Influenza A/Hongkong/1/68 to the 'master cleavage site', the sequence of the 3'-primer employed was (SEQ ID NO:3) 5'-ATGATGAGG-CCTCTTTTTTTTCTCTTTTTCTCTGGTACATTCCGC-A-3', wherein the nucleotide sequence (SEQ ID NO:5) TCT TTT TTT TCT CTT TTT is the reverse complement sequence of the sequence AAA AAG AGA AAA AAA AGA-3' (SEQ ID NO:6) that encodes the desired amino acid sequence, KKRKKR (SEQ ID NO:4) which replaces the original cleavage site, KQTR (SEQ ID NO:7). Upstream of this nucleotide sequence, the 3'-primer carried a StuI restriction site, which allowed its fusion to the 3'-portion of the HA cDNA. The 5'-primer, (SEQ ID NO:1), was the same as the 5'-primer employed for cloning as described above, that is, it did not carry any mutations with regard to Influenza A/Hongkong/1/68 and at its 5'-terminus it carried a XbaI restriction site.

The PCR-product was isolated and trimmed with the appropriate restriction enzymes (XbaI and StuI). The pUC19-HA vector carrying the HA cDNA of Influenza A/Hongkong/1/68 was also digested with the restriction enzymes XbaI and StuI to remove the portion of pUC19-HA that corresponded to the PCR-product. Instead of this portion, the trimmed PCR-product was ligated into the plasmid. The StuI restriction site occurs naturally in the HA sequence of Influenza A/Hongkong/1/68. To verify successful mutagenesis, the PCR-product inserted into the pUC19-HA vector carrying the PCR-product was linearized by digestion with Ksp632I and transcribed from the T3-promoter to give a negative strand RNA representing the HA segment of Influenza A/Hongkong/1/68 having an altered HA cleavage site of the amino acid sequence KKRKKR. Employing the ribonucleoprotein (RNP) transfection system according to Luytjes et al., "Amplification, Expression, and Packaging of a Foreign Gene by Influenza Virus", Cell, 59:1107–1113 (1989), an Influenza A/Hongkong/1/68 carrying the KKRKKR HA cleavage site was amplified in MDCK cells. In contrast to the method of Palese et al., no selection system was required since selection automatically preferred the more efficient cleavage site. Moreover, because there was no difference between the two types of virus other than the HA cleavage site, the two viruses, the original and the mutated version, belonged to the same serotype. The presence of the master cleavage site in the modified Influenza virus strain Influenza A/Hongkong/1/68 was confirmed by nucleotide sequencing on an Applied Biosystems 373 DNA Sequencer.

These data demonstrate that there was no significant difference in the HAI and ELISA antibody titres generated by immunization with the Brazil strain grown by standard egg technology or by the claimed method of this invention.

The description, tables and examples provided herein, while indicating preferred embodiments of the invention, are given by way of illustration and are not intended to limit the present invention. Various changes and modifications within the spirit and scope of the invention will become apparent to those skilled in the art upon reading the instant specification.

What is claimed is:

1. A method for producing virus antigens acceptable for human administration, comprising the steps of:
   (a) providing a culture of a continuous cell line of monkey kidney cells;
   (b) growing said cells for more than one generation in medium which is free of serum so that the cells can adapt to serum-free conditions;
   (c) infecting said culture of step (b) with a virus from the family Orthomyxoviridae; and
   (d) incubating said cell culture infected with said virus to propagate said virus into said medium to produce said virus antigens.

2. The method according to claim 1, wherein during step b) said cells are grown in said medium for at least six generations.

3. The method according to claim 1, wherein during step b) said cells are grown in said medium for at least twelve generations.

4. The method according to claim 1, wherein during step b) said cells are grown in said medium for at least eighteen generations.

5. The method according to claim 1, wherein during step b) said cells are grown in said medium for at least twenty-four generations.

6. The method according to claim 1, wherein said cells are chosen from the group of cell lines consisting of VERO, CV-1, and LLC-MK2 cell lines.

7. The method according to claim 1, wherein said virus is an Influenza virus.

8. The method according to claim 6, wherein said cells are VERO cells.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

ATGATGTCTA GAAGCAAAAG CAGGGGATAA TTC        33

( 2 ) INFORMATION FOR SEQ ID NO:2:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

ATGATGCTGC AGTTTAGTGA GGGTTAATAG TAGTAACAAG GGTGTTTT        48

( 2 ) INFORMATION FOR SEQ ID NO:3:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

ATGATGAGGC CTCTTTTTTT TCTCTTTTTC TCTGGTACAT TCCGCA        46

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

Lys Lys Arg Lys Lys Arg
1               5

( 2 ) INFORMATION FOR SEQ ID NO:5:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

TCTTTTTTTT CTCTTTTT        18

( 2 ) INFORMATION FOR SEQ ID NO:6:

( i ) SEQUENCE CHARACTERISTICS:
        ( A ) LENGTH: 18 base pairs

```
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

AAAAAGAGAA AAAAAAGA                                                      1 8

( 2 ) INFORMATION FOR SEQ ID NO:7:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:7:

Lys Gln Thr Arg
    1
```